US00PP29740P3

(12) United States Plant Patent
Sakuta et al.

(10) Patent No.: US PP29,740 P3
(45) Date of Patent: Oct. 9, 2018

(54) SHIITAKE MUSHROOM PLANT NAMED 'HOKSY 8'

(50) Latin Name: ***Lentinula edodes* (Berk.)**
Varietal Denomination: HOKSY 8

(71) Applicant: HOKUTO CORPORATION, Nagano (JP)

(72) Inventors: Genki Sakuta, Nagano (JP); Yurie Kaku, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 114 days.

(21) Appl. No.: 15/330,035

(22) Filed: Jul. 28, 2016

(65) Prior Publication Data

US 2017/0215316 P1 Jul. 27, 2017

(30) Foreign Application Priority Data

Jan. 25, 2016 (JP) ..... PBR 30787

(51) Int. Cl.
*A01H 15/00* (2006.01)

(52) U.S. Cl.
USPC ..... Plt./394

(58) Field of Classification Search
USPC ..... Plt./394
See application file for complete search history.

(56) References Cited

PUBLICATIONS

UPOV hit on Shitake mushroom named 'Hoksy 8Gokin', JP PBR 30787, filed Jan. 25, 2016.*

* cited by examiner

*Primary Examiner* — Anne Marie Grunberg
(74) *Attorney, Agent, or Firm* — Konomi Takeshita

(57) ABSTRACT

The present variety of mushroom plant named 'HOKSY 8' was cultivated by the gathering and repeated breeding of Shiitake mashrooms having dominant traits, which has good qualitative character and appearance, low malformation rates, hardly breakable lamella, and enhanced cultivation. This edible mushroom is exquisite in stability, reproducibility and uniformity when being produced.

9 Drawing Sheets

BACKGROUND OF THE INVENTION

This invention relates to a new and distinct variety of mushroom plant of Shiitake mushroom, *Lentinula edodes* (Berk.) Pegler. This new variety named 'HOKSY 8' cultivated by repeated breeding of Shiitake mushrooms having dominant traits, which has low malformation rates, hardly breakable lamella, and enhanced cultivation stability and ensures presentable stability, reproducibility, and uniformity.

Shiitake mushroom is an edible mushroom having the highest amount of production in Japan, which accounts for 69.1 billion yen as fresh shiitake mushrooms and 9.2 billion yen as dry shiitake mushrooms according to statistics in 2014. However, since those who engage in the production of shiitake mushrooms are mainly subsistence farmers, the supply of shiitake mushrooms is influenced by weather and the like, and therefore it is difficult to stably supply shiitake mushrooms. Accordingly, there is a strong demand in the market for the stable supply of shiitake mushrooms by our company, and therefore our company has been conducting a wide variety of studies for the stable production of shiitake mushrooms. Our company has developed a 'HOKSY 3' mushroom, which is excellent at cultivation property and has white stipe and lamella. Nevertheless, the 'HOKSY 3' mushroom has many problems in terms of quality in that its malformation rate is high and the lamella tends to be broken when the size of its pileus become large.

As a result of continuing breed improvement by cross breeding so as to improve the abovementioned problems and further enhance cultivation stability, a 'HOKSY 8' mushroom was developed that was improved in terms of the malformation rates and the lamella liable to be broken, as compared with the 'HOKSY 3' mushroom, and had higher cultivation stability than the 'HOKSY 3' mushroom.

SUMMARY OF THE INVENTION

The present invention is a new and distinct variety of mushroom characterized particularly by its good qualitative character and appearance, low malformation rates, hardly breakable lamella, and enhanced cultivation, which can be cultivated by gathering and repeated breeding of fungal strains having dominant traits and is exquisite in stability, reproducibility and uniformity when being produced. This novel and distinct variety of mushroom is identified as 'HOKSY 8'.

DETAILED DESCRIPTION OF THE INVENTION

The history of the 'HOKSY 8' mushroom in terms of improvement period and the like are set forth in the following chronological list of each stage of variety improvement:

July 1986: Cultivation of 'MH009094' strain.

January 1988: Cultivation of 'MH009095' strain.

1992: 'MH009094' strain and 'MH009095' strain were crossed and 'MH009096' strain was obtained.

September 2005: Cultivation of 'MH009074 (JMS 5K-16)' strain.

April 2008: 'MH009074' strain and 'MH009096' strain were crossed and 'MH009097' strain was obtained.

January 2009: Cultivation of 'MH009087' strain.

February 2010: 'MH009087' strain and 'MH009097' strain were crossed and 'MH009098' strain was obtained.

September 2011: 'MH009092 (HOKSY 3)' strain and 'MH009098' strain were crossed and 'MH009105' strain was obtained.

February 2012: Cultivation of 'MH009104' strain.

March 2014: 'MH009104' and 'MH009105' were crossed and an excellent strain 'MH009106' was picked.

January 2016: Growing test was repeatedly conducted on 'MH009106' and the distinguishability, stability and uniformity were confirmed, upon which the strain was named 'HOKSY 8' and cultivation was completed. Applied for registration of new variety to Ministry of Agriculture, Forestry and Fisheries of Japan.

Figure 1:
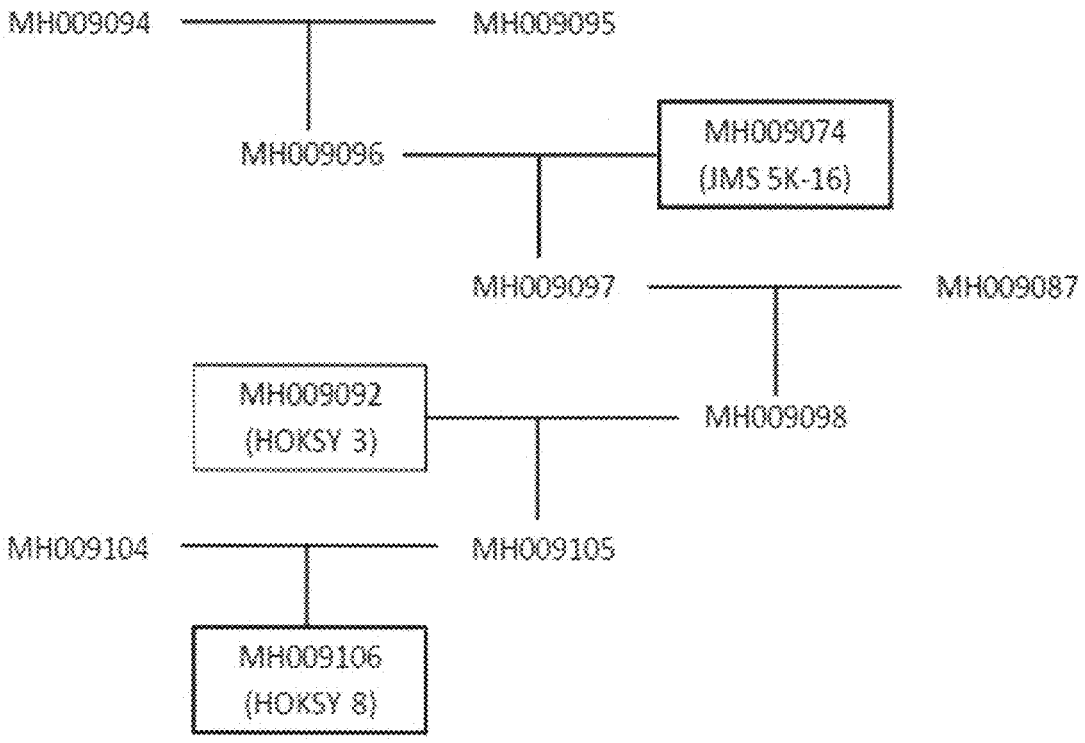
FIG. 1 shows a phylogenetic tree illustrating the antecedents of 'HOKSY 8' and 'JMS 5K-16' strains.

The above crossing is summarized in the phylogenetic tree illustrated in FIG. 1.

The 'HOKSY 8' mushroom has the following characteristics: low malformation rates, hardly breakable lamella, and enhanced cultivation.

(1) Comparison with Existing Variety by Dual Culture

Dual culture was performed for the 'HOKSY 8' mushroom and a similar variety so as to examine whether or not a zone line is formed.

Study Method:

As an examination method, a potato dextrose agar medium was used, and the 'HOKSY 8' mushroom and the similar variety were inoculated thereon face to face at an interval of 3 cm, and then culture was performed at 25° C. for 28 days to examine whether or not a zone line was formed.

Strain Used:

'HOKSY 8': Present variety

'JMS 5K-16' strain: Variety similar to the present variety

Figure 2B:
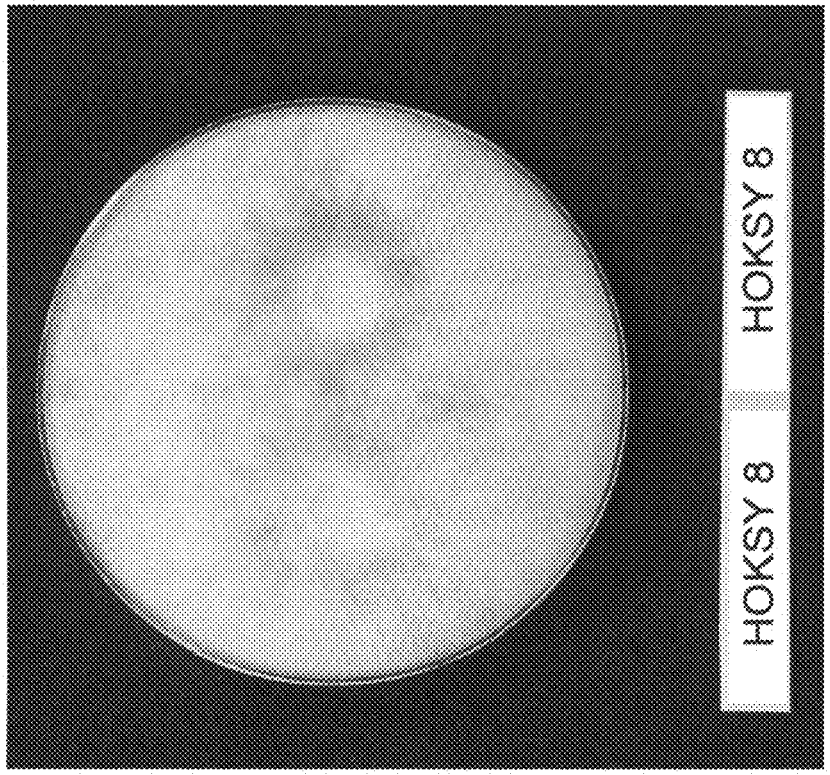
FIGS. 2A and 2B respectively show front and back images of a dual-culture of 'HOKSY 8' colony.
Figure 2A:
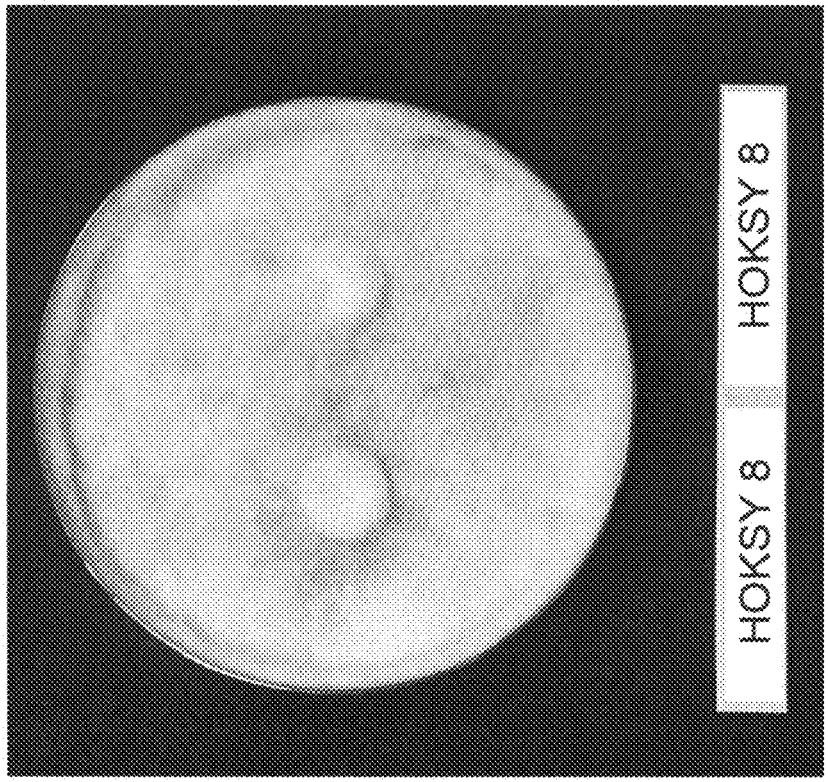
Figure 3B:
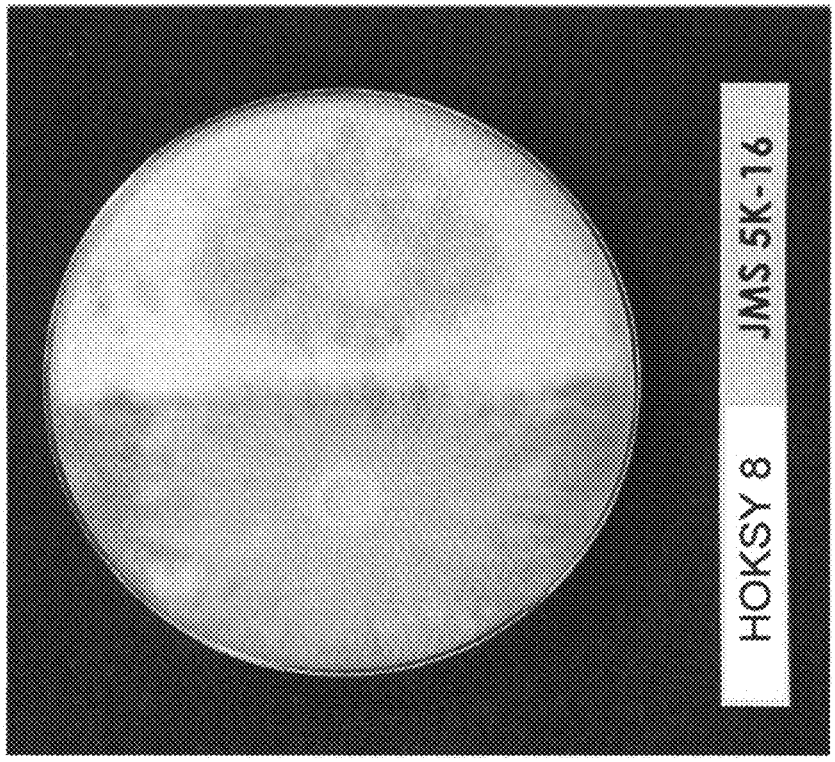
FIGS. 3A and 3B respectively show front and back images of a dual-culture of 'HOKSY 8' and 'JMS 5K-16' strains.
Figure 3A:
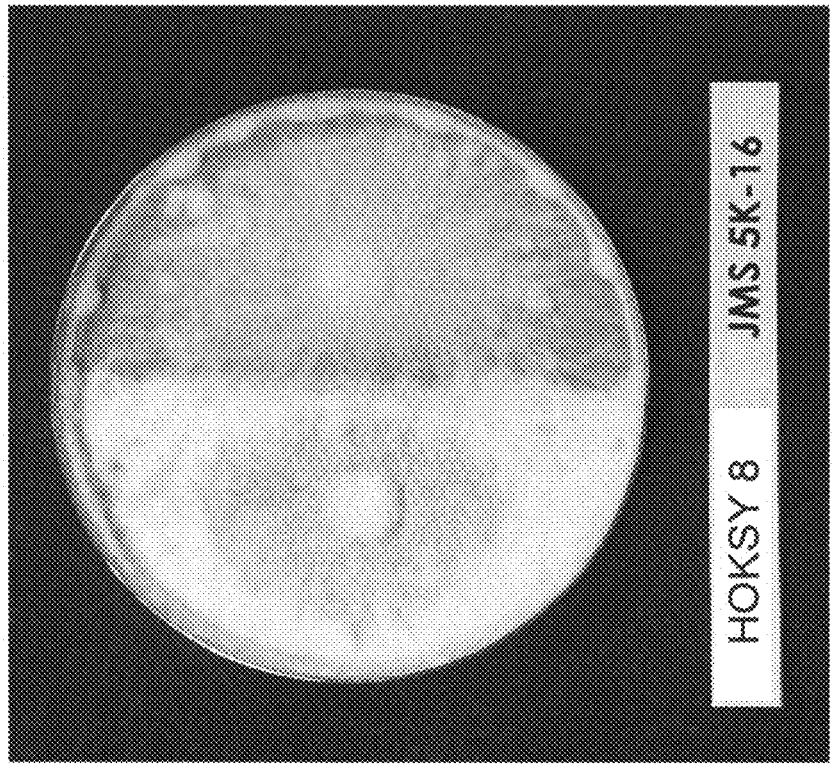

Results:

No zone line was formed in the dual culture of 'HOKSY 8' strains (Table 1, FIG. 2), while a zone line was formed between the 'HOKSY 8' and 'JMS 5K-16' strains (Table 1, FIG. 3). This clearly shows that the present mushroom is a new variety.

TABLE 1

| Results of dual culture | | |
|---|---|---|
| | Similar variety JMS 5K-16 strain | Present variety HOKSY 8 strain |
| HOKSY 8 | + | – |

+ is present and – is absent.

(2) Growth Characteristics of 'HOKSY 8'

(2)-1 Temperature Adaptation of Hyphae

Study Method:

After inoculating an agar piece of the 'HOKSY 8' having a diameter of 5 mm and an agar piece of the similar variety having a diameter of 5 mm on a potato dextrose agar medium, preculture was performed at 25° C. for 4 days so as to make the regeneration of hyphae equal (about 10 mm in diameter), and then culture was performed for 7 days at intervals of 5° C. between 5° C. and 30° C. An average daily hyphae growth rate was calculated based on a hyphae growth rate for seven days of the culture.

Results:

The hyphae elongation rate of the 'HOKSY 8' mushroom was lower than that of the similar variety at 5° C. (Table 2). The average hyphae growth rate of the 'HOKSY 8' mushroom was also lower than that of the similar variety at 30° C. (Table 2).

(2)-2 Comparison in the Formation of Hyphae Tunic, Aerial Hyphae and Tinting of the Surface of Fungal Flora Study Method:

After inoculating an agar piece of the 'HOKSY 8' having a diameter of 5 mm and an agar piece of the similar variety having a diameter of 5 mm on a potato dextrose agar medium, culture was performed at 25° C. for 14 days. For these two strains, comparative observation was performed with regard to hyphae tunic, aerial hyphae and tinting of the surface of fungal flora.

Figure 4:
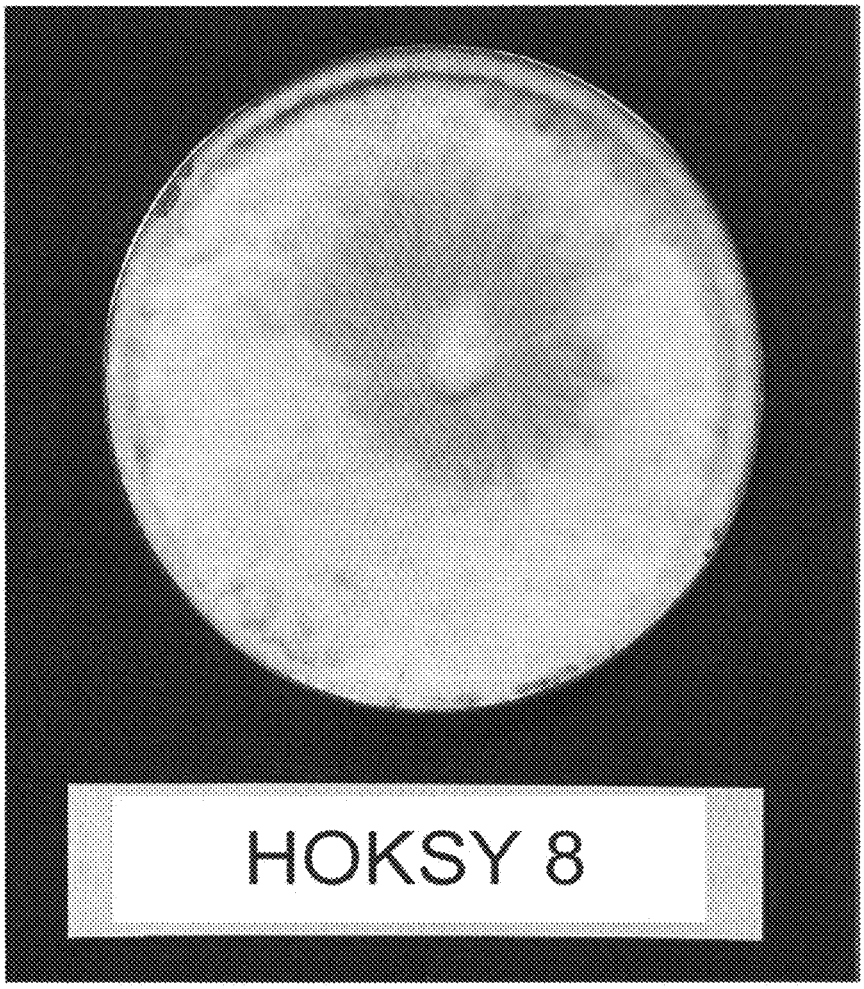
FIG. 4 shows an image of the surface of fungal flora of 'HOKSY 8'.
Figure 5:
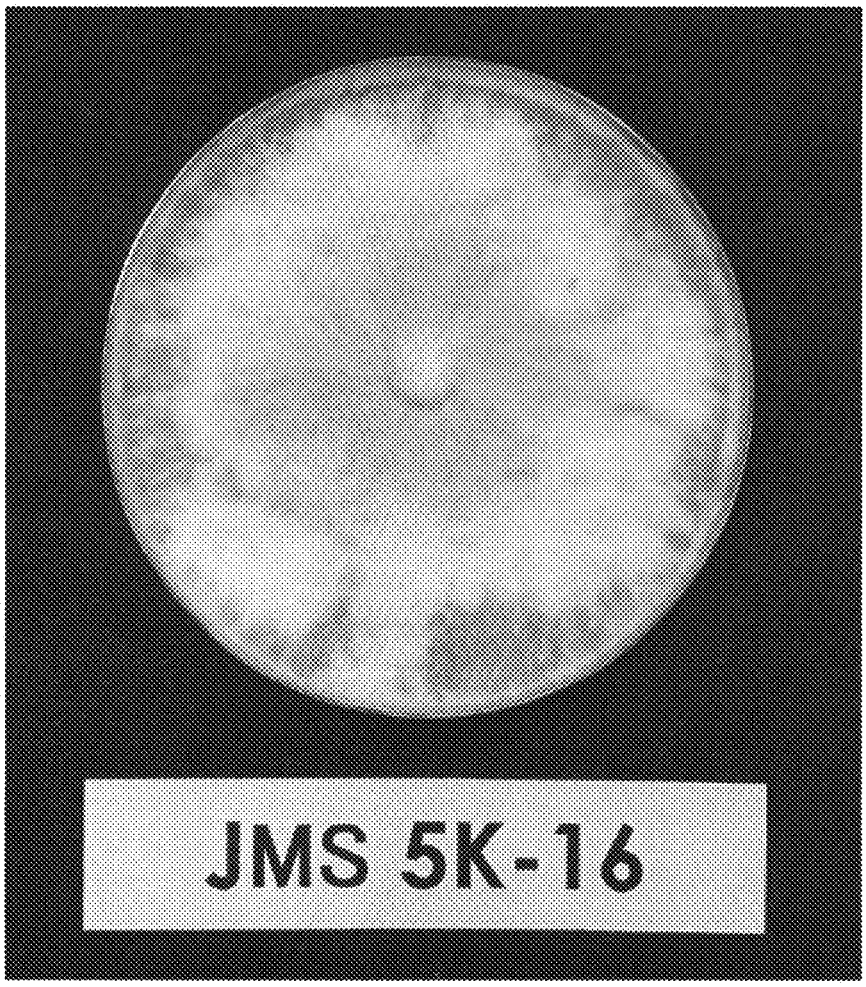
FIG. 5 shows an image of the surface of fungal flora of 'JMS 5K-16'.
Figure 6:
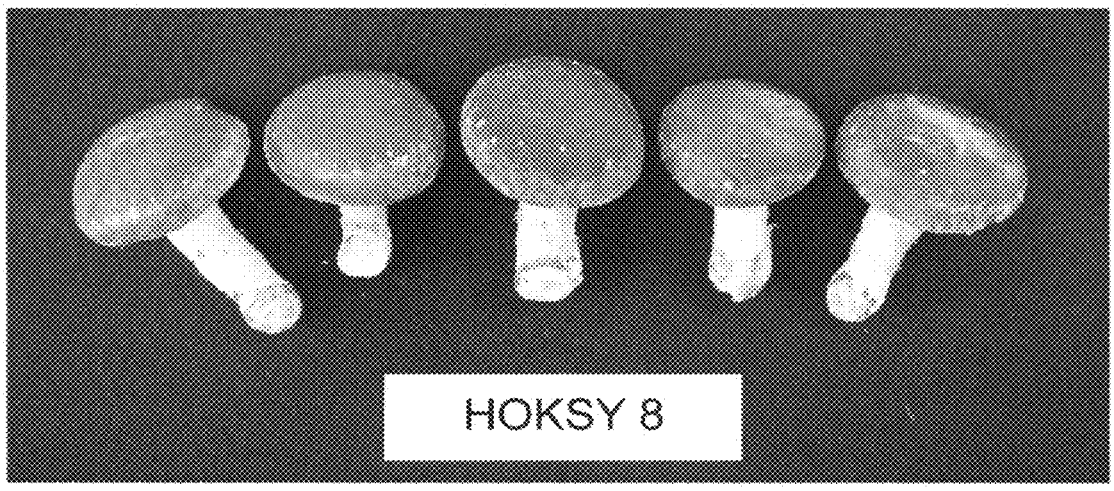
FIG. 6 shows an image of a fruit body of 'HOKSY 8'.
Figure 7:
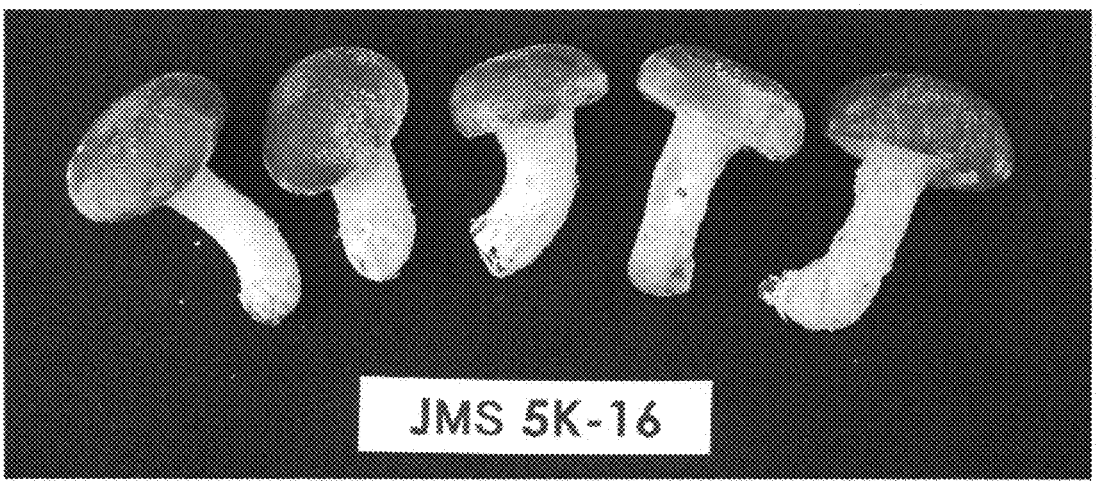
FIG. 7 shows an image of a fruit body of 'JMS 5K-16'.
Figure 8A:
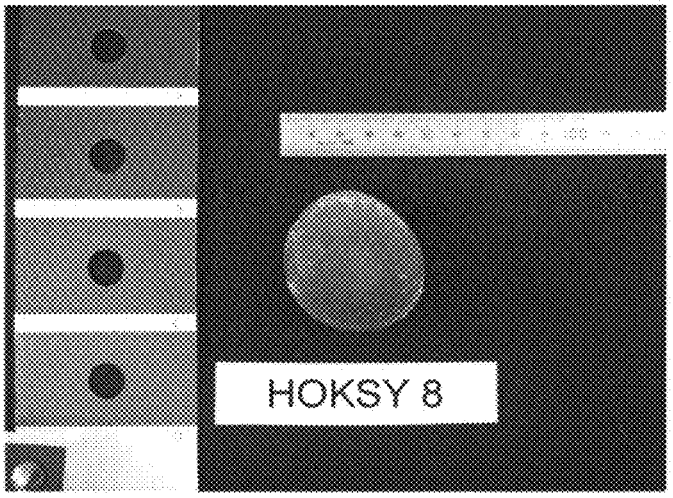
FIGS. 8A, 8B, and 8C respectively show top, underside, and cross-sectional images of a fruit body of 'HOKSY 8'.
Figure 8B:
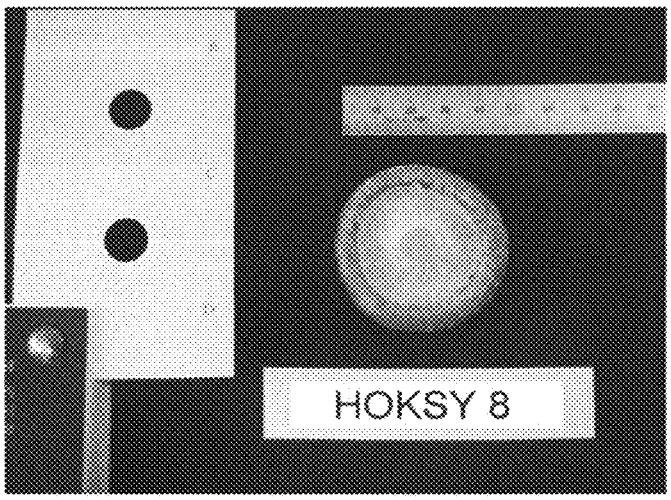
Figure 8C:
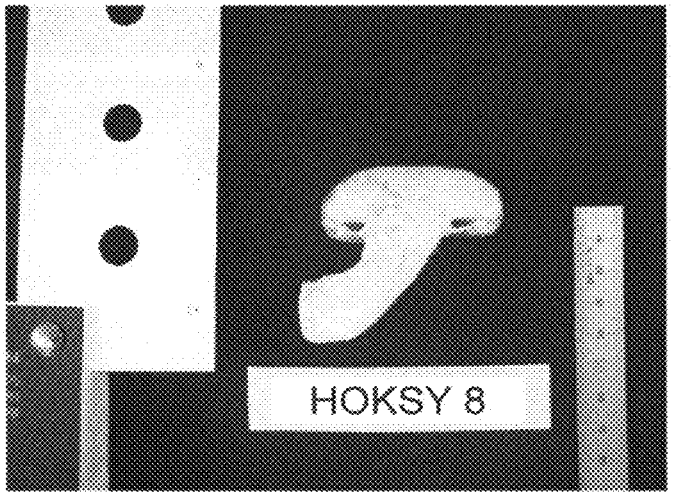
Figure 9A:
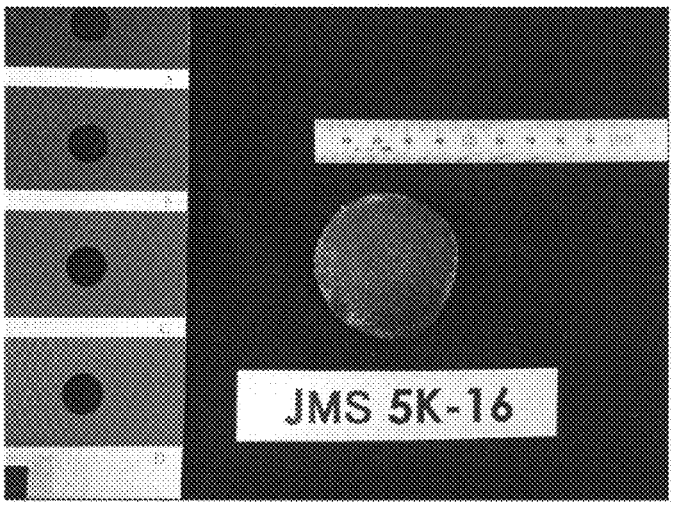
FIGS. 9A, 9B, and 9C respectively show top, underside, and cross-sectional images of a fruit body of 'JMS 5K-16'.
Figure 9B:
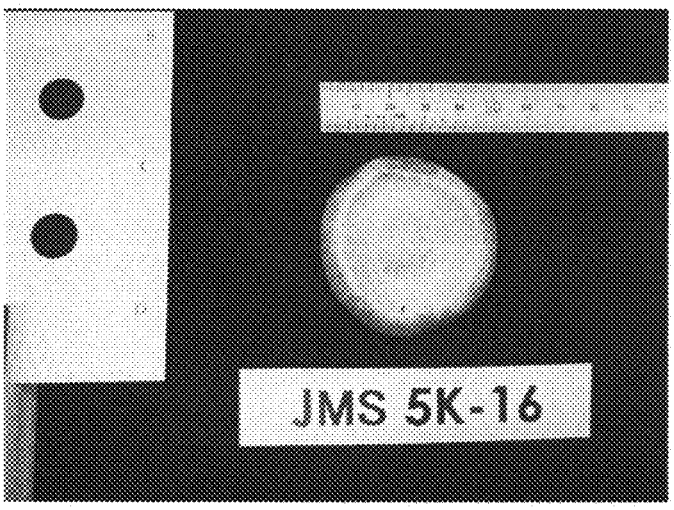
Figure 9C:
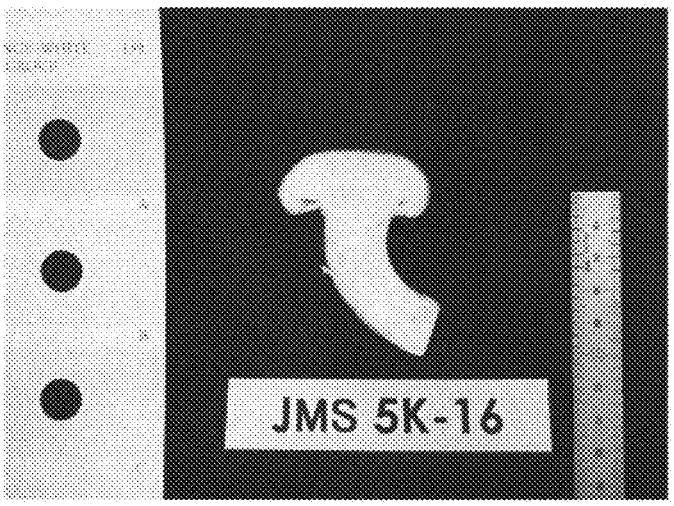

Results:

The formation of hyphae tunic was confirmed in the 'HOKSY 8' mushroom, while it was not confirmed in the similar variety (Table 2). With regard to aerial hyphae, the 'HOKSY 8' mushroom had more than the similar variety (Table 2). The tinting of the surface of fungal flora was observed in the 'HOKSY 8' mushroom, while it was not confirmed in the similar variety (Table 2, FIGS. 4 and 5).

(3) Morphological Characteristics of the 'HOKSY 8' Mushroom in a Cultivation Example Cultivation Method:

Mushroom bed bag: A mushroom bed bag made of polyethylene (117 mm×230 mm, 35φ) was used.

Culture medium: Sawdust, rice bran and wheat bran were mixed at the dry weight ratio of 8:1:1, and the water content was adjusted to 63%. The amount of a medium filled was 1.5 kg per bag, and high-pressure sterilization was performed.

Starter culture: About 20 mL of sawdust starter cultures per bottle was inoculated.

Culture: Culture was performed at 20° C. for 85 days at 60-70% moisture.

Growth: After completing the culture, the mushroom bed was taken out of the bag and washed with water, and then mushrooms were grown at 13-14° C., at 90% moisture or higher at a CO2 concentration of 1,000 ppm or lower. An immersion method was used as the generation method on the second time and thereafter.

Cultivation Results:

Table 2 shows the characteristics of the 'HOKSY 8' and specific difference in characteristics as compared with the similar variety when culture was performed under the abovementioned conditions.

Also, the whole, top, underside, and cross-sectional images of the respective fruit bodies have also been attached. (Refer to FIGS. 6 to 9).

TABLE 2

Fungus characteristics Table of *Lentinula edodes* (Berk.) Pegler of Recording and Registration

| | Present variety HOKSY 8 | Similar variety JMS 5K-16 |
|---|---|---|
| Physiological property | | |
| Formation of hyphae tunic | + | – |
| Aerial hyphae development | much | medium |
| Density of hyphae | medium | medium |
| Tinting of surface of fungal flora | + | – |
| Accommodatuveness for temperature | | |
| Tolerance to hight temprature or low temprature | There is no significant | |
| Optimal temperature for hyphal growth (° C.) | 26 | 26 |
| Hyphal growth rate at each temperature (mm/day) | | |
| 5° C. | 0.43 | 0.87 |
| 10° C. | 1.74 | 1.63 |
| 15° C. | 2.68 | 3.15 |
| 20° C. | 4.09 | 4.27 |
| 25° C. | 4.85 | 4.54 |
| 30° C. | 1.98 | 2.73 |
| Morphological property | | |
| Cap | | |
| Shape of top view | round | round |
| Shape of vertical cross section | concave | concave |
| Fleshy type | type 1 | type 1 |
| Diameter (mm) | 43.91 | 38.11 |
| Main color of apex | brown [RHS:200C] | brown [RHS:202C] |
| Thickness (mm) | 11.08 | 7.74 |
| Hardness | medium | medium |
| Distribution of scales | periphery | periphery |
| Size of scales | medium | medium |
| Gill | | |
| Shape | type 1 | type 2 |
| Arrangement | ripple or crinkle | straight |

TABLE 2-continued

Fungus characteristics Table of *Lentinula edodes* (Berk.) Pegler of Recording and Registration

| | Present variety HOKSY 8 | Similar variety JMS 5K-16 |
|---|---|---|
| Width (mm) | 0.88 | 1.00 |
| Density | sparse | medium |
| Color | cream [RHS:159D] | cream [RHS: 159D] |
| Stipe | | |
| Shape | type 1 | type 1 |
| Length (mm) | 39.70 | 42.44 |
| Ratio of cap diameter/stipc length | 1.01 | 1.00 |
| Thickness (mm) | 12.36 | 13.68 |
| Ratio of cap diameter/stipe thickness | 3.61 | 2.98 |
| Tinting | + [RHS:159B] | + [RHS:159B] |
| Presence of fluff | + | + |
| Tinting of fluff | + [RHS:159B] | + [RHS:159B] |
| Hardness | hard | hard |
| Cultural property | | |
| Period from inoculation to fruit induction (day) | 85 | 85 |
| Period from fruit induction to harvest (day) | 11.3 | 12.3 |
| Type of fruiting | concentrated | concentrated |
| Soaking yield | fitness | fitness |
| Temperature of soaking yield (° C.) | 14 | 14 |
| Method of secondary fruiting | use jointly | use jointly |
| Fruiting temperature (° C.) | 14 | 14 |
| Adaptability of culture medium | broad leaved | broad leaved |
| Ratio of dry weight fruit body (%) | 9.0 | 10.4 |
| Average of 1 dry weight fruit body (g) | 2.3 | 2.0 |
| Yield | | |
| Yield of sawdust medium 100 kg (kg) | 3.55 | 3.87 |
| Ratio of every month yield (%) | | |
| 1st month | 55.97 | 61.36 |
| 2nd month | 14.49 | 8.68 |
| 3rd month | 15.78 | 13.35 |
| 4th month | 13.76 | 16.61 |

* The employed color chart is R.H.S Colour Chart, 2007, Fifth edition, prescribed by Royal Horticultural Society, England.

What is claimed is:

1. A new, distinct variety of Shiitake mushroom plant as substantially illustrated and described in the specification.

* * * * *